US009480822B2

(12) United States Patent
Kaiser (10) Patent No.: US 9,480,822 B2
(45) Date of Patent: Nov. 1, 2016

(54) LOCKING DEVICE

(71) Applicant: HOLOGIC, INC., Marlborough, MA (US)

(72) Inventor: Christopher Charles Kaiser, Holliston, MA (US)

(73) Assignee: Hologic, Inc., Bedford, MA (US)

( * ) Notice: Subject to any disclaimer, the term of this patent is extended or adjusted under 35 U.S.C. 154(b) by 506 days.

(21) Appl. No.: 14/139,244

(22) Filed: Dec. 23, 2013

(65) Prior Publication Data

US 2015/0174372 A1   Jun. 25, 2015

(51) Int. Cl.
| A61M 5/32 | (2006.01) |
| A61M 25/02 | (2006.01) |
| A61B 1/00 | (2006.01) |
| A61M 25/01 | (2006.01) |
| A61M 25/09 | (2006.01) |

(52) U.S. Cl.
CPC .......... *A61M 25/02* (2013.01); *A61B 1/00147* (2013.01); *A61M 25/013* (2013.01); *A61M 2025/0213* (2013.01); *A61M 2025/09116* (2013.01); *A61M 2025/09125* (2013.01)

(58) Field of Classification Search
CPC ......... A61M 25/09041; A61M 25/09; A61M 2025/09116; A61M 2025/09125; A61M 25/0606
USPC ............................ 604/174–180, 158, 164.01
See application file for complete search history.

(56) References Cited

U.S. PATENT DOCUMENTS

| 3,730,187 | A | 5/1973 | Reynolds |
| 4,860,742 | A | 8/1989 | Park et al. |
| 5,325,868 | A | 7/1994 | Kimmelstiel |
| 5,707,357 | A | 1/1998 | Mikhail et al. |
| 5,746,722 | A | 5/1998 | Pohndorf et al. |
| 7,458,964 | B2 | 12/2008 | Mosler et al. |
| 7,959,611 | B2 | 6/2011 | Harvey et al. |
| 2007/0219467 | A1* | 9/2007 | Clark ................. A61M 25/0113 600/585 |
| 2008/0147011 | A1 | 6/2008 | Urmey |
| 2010/0022917 | A1* | 1/2010 | Landowski ..... A61M 25/09041 600/585 |

FOREIGN PATENT DOCUMENTS

EP      2052756      10/2007

OTHER PUBLICATIONS

PCT International Search Report and Written Opinion for International Application No. PCT/US2014/063901, Applicant Hologic, Inc., forms PCT/ISA/210, 220, and 237, dated Mar. 20, 2015 (13 pages).

\* cited by examiner

*Primary Examiner* — Phillip Gray
(74) *Attorney, Agent, or Firm* — Vista IP Law Group LLP (57) ABSTRACT

A slidable locking device for fixing a position of a medical device, includes a housing having a passageway therethrough and an actuator coupled to the housing movable between a locked position and an unlocked position. The actuator includes at least two arms extending therefrom that are operatively coupled with at least two engaging members disposed within the housing, each engaging member having a slot configured to receive a respective arm of the actuator, the engaging members being biased towards the housing passageway, wherein the engaging members are disposed toward the housing passageway when the actuator is in the locked position, and the engaging members are disposed away from the housing passageway when the actuator is in the unlocked position.

17 Claims, 12 Drawing Sheets

LOCKING DEVICE

FIELD OF THE INVENTION

The disclosed inventions pertain generally to position-locking devices for elongated medical tubular members, such as catheters and probes.

BACKGROUND

The use of medical catheters and probes has become an effective method for treating many types of diseases. In general, a suitable catheter or tubular probe is inserted into a body lumen of the patient (vascular or non-vascular) and navigated through the body lumen into a desired target site. Using this method, virtually any target site in the patient's body may be accessed. In certain treatments, it is desirable to secure the catheter or probe in some manner so that proper positioning and placement is maintained during the treatment, while the patency the catheter or probe lumen is also maintained, such as in some urinary incontinence treatments.

Urinary incontinence is one of the most prevalent conditions of the lower urinary tract, particularly, stress urinary incontinence (hereinafter SUI) which affect a significant amount of people. SUI is the loss of small amounts of urine associated with movements, such as coughing, sneezing, laughing, and exercise that cause increased pressure on the bladder based on increased intra-abdominal pressure. Some SUI treatments include the delivery of energy to and/or through the urethral wall by precisely placing an elongated probe having an energy delivery element within the urinary tract. These probes usually have an anchoring member, such as an inflatable balloon, at a distal portion of the probe that sits in a patient's bladder, and a locking device at the proximal portion of the probe that is placed against the patient's external urethral orifice, urinary meatus and/or adjacent tissue, thereby securing the probe and the energy delivery member in a desirable position within the urethra. During these treatments, minimizing movement of the probe relative to the desired treatment site in the urethra and/or paraurethral region, as well as, maintaining patency of the probe lumen, is desirable.

In the past, various devices have been used for securing the positioning of a catheter or probe relative to a treatment site, such as locking collars, seals, claps, and compression sleeves. While these types of locking devices may secure the positioning and placement of a catheter or probe in combination with anchoring members, they also cause localized cramping, pinching, compression or deformation of the catheter or probe tubular body, radially narrowing or even occluding the lumen of the catheter or probe. Additionally, once these locking devices are engaged or locked in place on or over a catheter or probe, disengaging or unlocking the device for repositioning requires transmission of an undesirable amount axial translation force, radial force and/or friction to the catheter or probe, usually displacing the catheter or probe relative to a treatment site. Further, some of these devices have cumbersome locking mechanism, often requiring the use of both hands of a physician or user to unlock and reposition the device.

Therefore, there is an ongoing need to provide for more suitable adjustable locking devices that minimize friction, axial translation or radial forces to the catheter or probe during advancement and placement, as well as, during unlocking and repositioning of the device, which requires only one hand of a user to fully operate the locking mechanism.

SUMMARY

In one embodiment of the disclosed inventions, a slidable locking device for use on a medical device includes a housing having a passageway therethrough, and an actuator coupled to the housing, wherein the actuator is movable between a locked position and an unlocked position. The actuator has at least two arms extending therefrom operatively coupled with corresponding engaging members disposed within the housing, each engaging member having a slot configured to receive a respective arm of the actuator, the engaging members being biased towards the housing passageway, wherein the engaging members are disposed toward the housing passageway when the actuator is in the locked position, and away from the housing passageway when the actuator is in the unlocked position.

By way of non-limiting example, the actuator is movable between the locked position and the unlocked position by an application of force in a range between about 1 lbf to about 3 lbf. Further, the actuator is movable from the unlocked position to locked position by an application of force of about 1.2 lbf, and the actuator is movable from the locked position to unlocked position by an application of force of about 2.4 lbf.

The slidable locking device may include a connector coupled between the housing and the actuator, wherein the connector defines a pivot axis and the actuator is configured to move about the pivot axis between the locked position and the unlocked position. The housing is an elongated housing having a first portion and a second portion, the first and second portions defining an internal cavity, and wherein the at least two engaging members are disposed within the cavity. Each of the engaging members includes one or more sloped mating surfaces defining the respective slot, and each arm of the actuator includes one or more protrusions, and wherein the one or more protrusions are configured to engage the respective one or more sloped mating surfaces. Each of the one or more protrusions of the engaging members may have a spherical, semi-spherical, or convex configuration. The one or more protrusions are configured to slide along the respective one or more sloped mating surfaces so that the actuator arms exert force against and thereby move the engaging members outwardly away from the housing passageway.

In accordance with another embodiment of the disclosed inventions, a medical device for treating a target site in a body of a patient includes an elongate member having a proximal portion, a distal portion, with a lumen extending therebetween, and a locking device slidably disposed on the elongate member. The locking device advantageously resists relative movement with respect to the elongate member when the actuator is in the locked position, and is configured to translate along the elongate member and to rotate about the elongate member when the actuator is in the unlocked position.

The locking device includes a housing having a passageway therethrough, and an actuator coupled to the housing. The actuator is movable between a locked position, wherein the locking device is engaged to the elongate member, to an unlocked position, wherein the locking device is disengaged from the elongate member. The actuator has at least two arms extending therefrom operatively coupled with corresponding engaging members disposed within the housing, each engaging member having a slot configured to receive a respective arm of the actuator, the engaging members being biased towards the housing passageway, wherein the engaging members are disposed toward the housing passageway when the actuator is in the locked position, and away from the housing passageway when the actuator is in the unlocked position.

Each of the engaging members includes one or more sloped mating surfaces defining the respective slot, and each arm of the actuator includes one or more protrusions, and wherein the one or more protrusions are configured to engage the respective one or more sloped mating surfaces. The one or more protrusions of the engaging members are configured to slide along the respective one or more sloped mating surfaces so that the actuator arms exert force against and thereby move the engaging members outwardly away from the housing passageway. The engaging members may include concave surfaces to engage an arcute surface the elongate member. The engaging members may include a compliant material configured to conform to a surface of the elongate member.

The locking device is preferably configured to apply a force to the elongate member in a range of about 10 PSI to about 40 PSI, and more preferably to apply a force in a range of about 12 PSI to about 17 PSI, when the actuator is in the locked position. The locking device is configured to distribute the applied force to the elongate member such that the lumen of the elongate member maintains patency. The locking device is configured to withstand an aggregate load in a range of between about 4 lbf to about 12 lbf, without any movement relative to the elongate member when the actuator is in the locked position.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. The relative scale of select elements may have been exaggerated for clarity. In order to better appreciate how the above-recited objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the inventions or as a limitation on the scope of the inventions, which are defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 1:
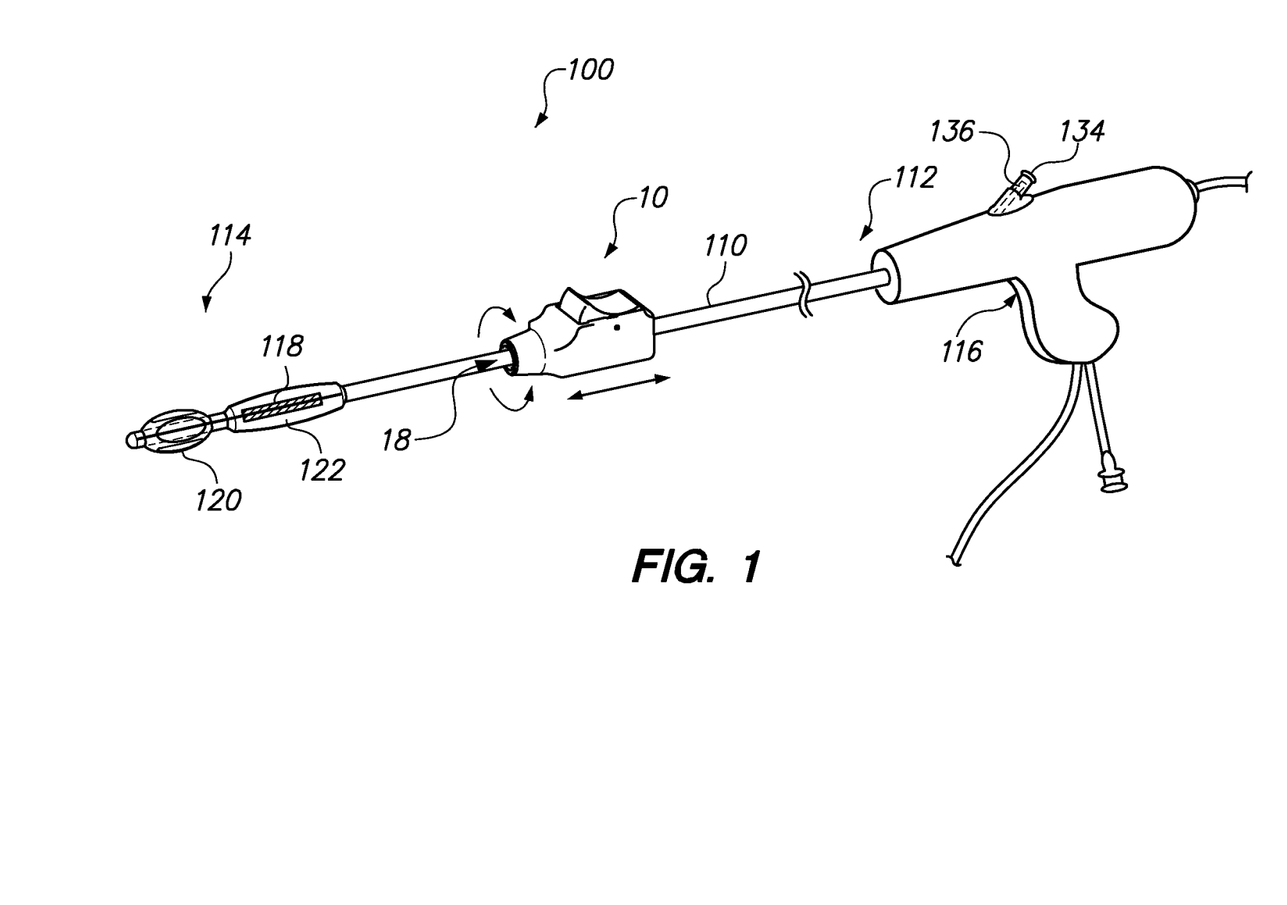
FIG. 1 is a plan view of a SUI assembly constructed according to one embodiment of the disclosed inventions.

FIG. 1 illustrates a SUI assembly 100 according to the disclosed inventions. The SUI assembly 100 includes an elongate member 110 having a proximal portion 112, a distal portion 114, and defining one or more inner lumens extending therebetween (not shown). The proximal portion 112 of the elongate member 110 is coupled to a handle 116. The distal portion 114 of the elongate member 110 includes an anchoring balloon 120, a cooling balloon 122 and an energy delivery member 118 (e.g. transducer) disposed within the cooling balloon 122. The one or more lumens of the elongate member 110 are in fluid communication with respective anchoring 120 and cooling 122 balloons for inflation and/or deflation of the balloons with fluid and/or gas. The structure of the SUI assembly 100 and the elongate member 110 allows fluid communication between a fluid port 134, a lumen (not shown) and the anchoring balloon 120. A seal 136 is included at the fluid port 134 to provide a fluid seal and maintain inflation or deflation of the anchoring balloon 120. The SUI assembly may be made of polymeric materials, such as polyethylene, or other suitable biocompatible materials or combinations thereof. As used in this specification, the term "elongate member" may refer to any member having a variety of elongated shapes, including a catheter, a tubular probe, a shaft, a needle, a wire, a sleeve, or any other configuration.

The SUI assembly 100 further includes an adjustable locking device 10 disposed around the elongate member 110. The adjustable locking device 10 includes a passageway 18 for allowing passage of the elongate member 110. For example, the passageway 18 may be an axial passageway or may be off-axis from the locking device 10. In a further example, the passageway 18 may have a diameter larger than the outer diameter of the elongate member 110 (FIG. 3B), when the locking device 10 is disengaged, so that, the locking device 10 slides over and/or rotates around the elongate member 110 with minimal friction or non-friction to the elongate member 110.

The adjustable locking device 10 is configured to be operated by a single hand of a physician or user to engage, disengage and move the device 10 along the length of the elongate member 110. The adjustable locking device 10 is configured to be engaged in a desired position along the elongate member 110, and is further configured to be disengaged and repositioned in different desirable positions along the elongate member 110 with the use of minimal force to engage and disengage the device 10. For example, the adjustable locking device 10 is configured to be engaged and disengaged with a range of force between 1 to 3 pound force (lbf); preferably, approximately 2.4 lbf to disengage and approximately 1.2 lbf to engage. When the locking device 10 is engaged and maintains a desired position along the elongate member 110, the locking device 10 is configured to withstand an aggregate load between 4 to 12 lbf while maintaining engagement to the elongate member 110. Further, the locking device 10 is configured to maintain the patency of the lumen or lumens of the elongate member 110 when engaged, and while withstanding aggregate load between 4 to 12 lbf. While the locking device 10 is engaged, the device 10 maintains relatively low localized compression on the elongate member 110, e.g. in a range between about 10 PSI and to about 40 PSI, and more preferably in a range between about 12 PSI to about 17 PSI, when the actuator is in the locked position, so as to avoid deformation of the elongate member 110. As used in this specification, the term "engaged" may refer to the adjustable locking device 10 being activated, actuated or in a locked position along the length of the elongate member 110, and the term "disengaged" may refer to the locking device 10 being deactivated, in an unlocked position, freely movable along the elongate member 110.

Figure 2:
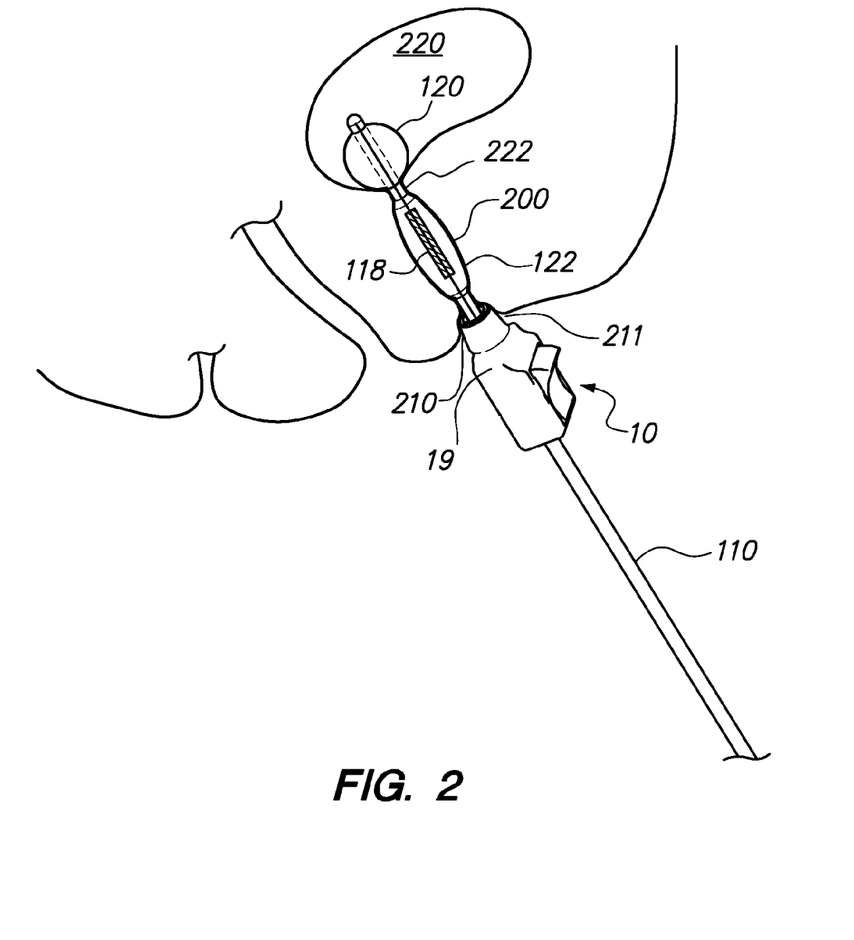
FIG. 2 is a cross-sectional view of an exemplary method of use of the SUI assembly of FIG. 1.

FIG. 2 illustrates an exemplary method of use of the assembly 100 of FIG. 1 for treatment of SUI in a female patient. After gaining access to a patient's urethra 200, the elongate member 110 is introduced until the anchoring balloon 120 is located in a bladder 220. The anchoring balloon 120 is then inflated and positioned at the neck 222 of the bladder 220, where the anchoring balloon 120 sits against the orifice of the interior of the bladder so that the energy delivery member 118, disposed within the cooling balloon 122, in positioned in the urethra 200 at a desired treatment site. The anchoring balloon 120 resists axial movement of the elongate member 110 relative to the anchoring balloon 120. When anchoring bladder 120 is inflated and positioned at the neck 222 of the bladder 220 and the elongate member 110 is pulled proximally, the anchoring balloon 120 resists cuffing. The adjustable locking device 10 is then advanced or distally moved along the elongate member 110 to press against the external urethral orifice/urinary meatus 210 and/or adjacent tissue 211 of a patient. Particularly, the locking device includes a distal end 19 shaped and sized to press against external urethral orifice/urinary meatus 210 and/or adjacent tissue 211.

The distal end 19 of the locking device is composed of any suitable polymeric material. Further, the distal end 19 may include conforming materials, such as foam or rubber, or may include one or more layers and/or coatings of conforming materials or combination thereof. For example, the distal end 19 of the locking device 10 may be pressed against the adjacent tissue 211 (e.g. approximately 0.5 inches from the orifice/meatus 210) without contacting or pressing against the urethral orifice/urinary meatus 210. When the adjustable locking device 10 is advanced and the distal end 19 presses against the external urethral orifice/urinary meatus 210 and/or adjacent tissue 211; then, the locking device 10 can be engaged with the elongate member 110 to thereby secure the elongate member 110 at the desired position. It will be appreciated that placement of the anchoring balloon 120 at the bladder 220 and engagement of the locking device 10 to the elongate member 110 provides a controlled securement and positioning of the energy delivery member 118 at the desired treatment site or position in the urethra 200. The adjustable locking device 10 further secures the energy delivery member 118 in the desired position or treatment site within the urethra 200 during the treatment of SUI, avoiding or minimizing displacement of the energy delivery member 118 relative to the treatment site. For example, if axial displacement of the energy delivery member 118 relative to the treatment site occurs, when the locking device 10 is engaged, it may be a minimal displacement; (e.g. approximately 2 millimeter). In a preferred embodiment, the locking device 10 is configured to apply about 12 PSI to about 17 PSI to the elongate member 110 when engaged, and is further configured to withstand an aggregate load in a range between 4 to 12 lbf while maintaining patency of the elongate member 110 lumen(s) and/or avoiding localized compression, deformation or otherwise occluding the elongate member 110 lumen(s). The locking device 10 is configured to be single-handily disengage, reposition and engage or re-engage, with minimal amount of force from a physician or user, for example, in a range between 1 to 3 pound force (lbf); preferably, approximately 1.2 lbf to engage and approximately 2.4 lbf to disengage. After the SUI treatment is completed (i.e. a desirable amount of energy delivered to the urethra 200 and/or to the parauretral region beyond the urethral wall), the anchoring 120 and cooling 122 balloons are deflated, the locking device 10 may be disengaged and moved proximally along the elongate member 110, and the SUI assembly 100 is withdrawn from the treatment site.

Although, the use of the adjustable locking device 10 is described in connection with the assembly 100 for treatment of male and female SUI, it will be appreciated that the adjustable locking device 10 may be used in connection with any other type of assembly, device, catheter, tubular probe, shaft or any other configuration of an elongate member.

Figure 3A:
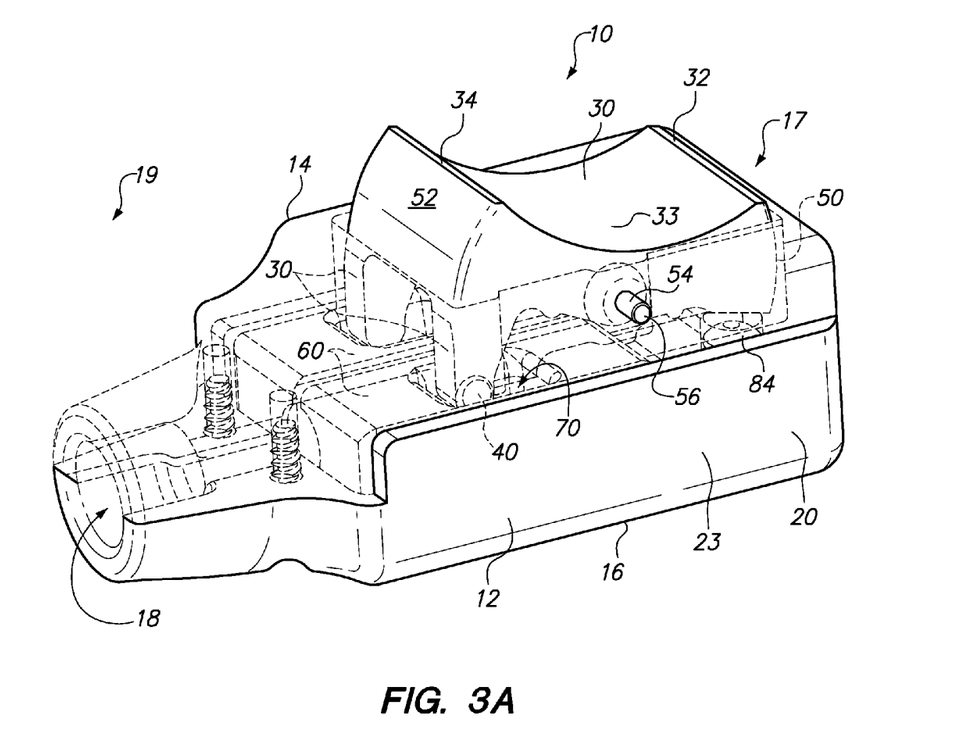
FIGS. 3A-B are perspective views of a locking device constructed according to one embodiment of the disclosed inventions.
Figure 3B:
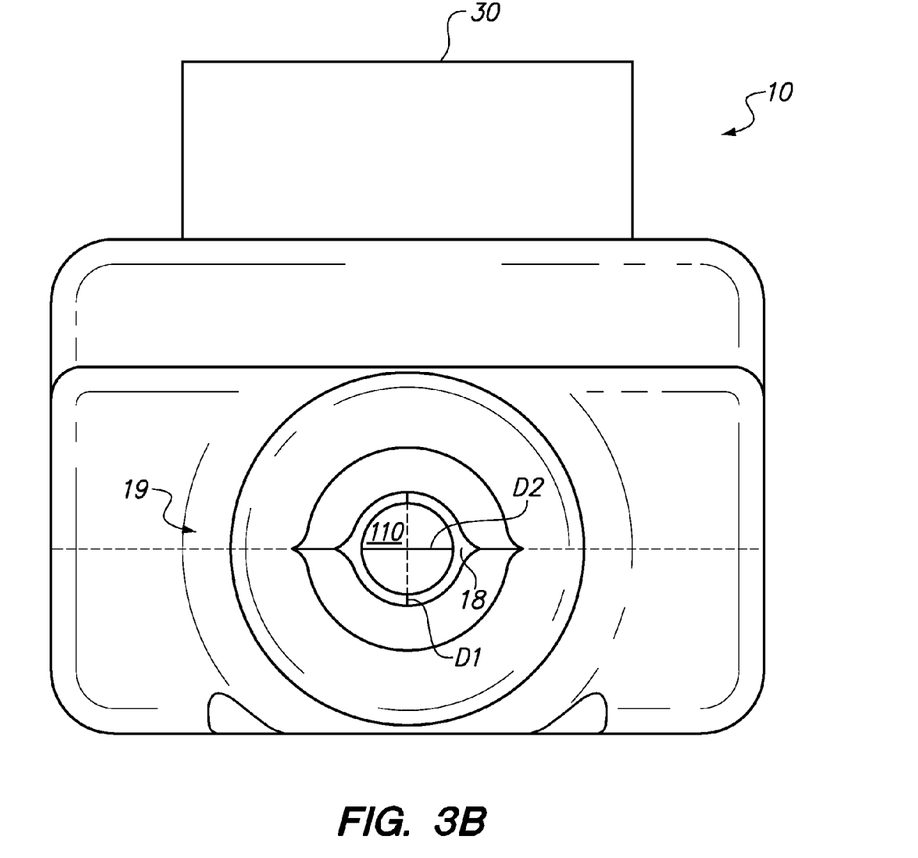

FIG. 3A illustrates the adjustable locking device 10 having a proximal end 17, the distal end 19, and a passageway 18 therethrough for allowing passage of the elongate member 110. The locking device 10 includes a housing 12 having a first (e.g. upper) portion 14 and a second (e.g. lower) portion 16. The locking device 10 further includes a connector 54 coupled to the housing 12 and an actuator 30, the connector 54 defining a pivot axis for the actuator 30. For example, the connector 54 is in the shape of an elongate pin having two ends 56 (FIG. 4), but the connector 54 may be in the shape of any suitable member or axle. The actuator 30 comprises a first position, where the locking device 10 is engaged with the elongate member 110, and a second position, where the locking device 10 is disengaged from the elongate member 110, allowing axial translation and/or rotational movements of the locking device 10 along and/or around the elongate member 110. FIG. 3B illustrates the adjustable locking device 10 distal end 19 and the passageway 18, having the elongate member 110 position within the passage 18. The passage 18 includes a diameter D1 larger than the outer diameter D2 of the elongate member 110, so that when the locking device 10 is disengaged, the locking device 10 translates along, slides over and/or rotates about the elongate member 110 with minimal friction or non-friction to the elongate member 110. Further components of the adjustable locking device 10 will be discussed in greater detail below.

Figure 4:
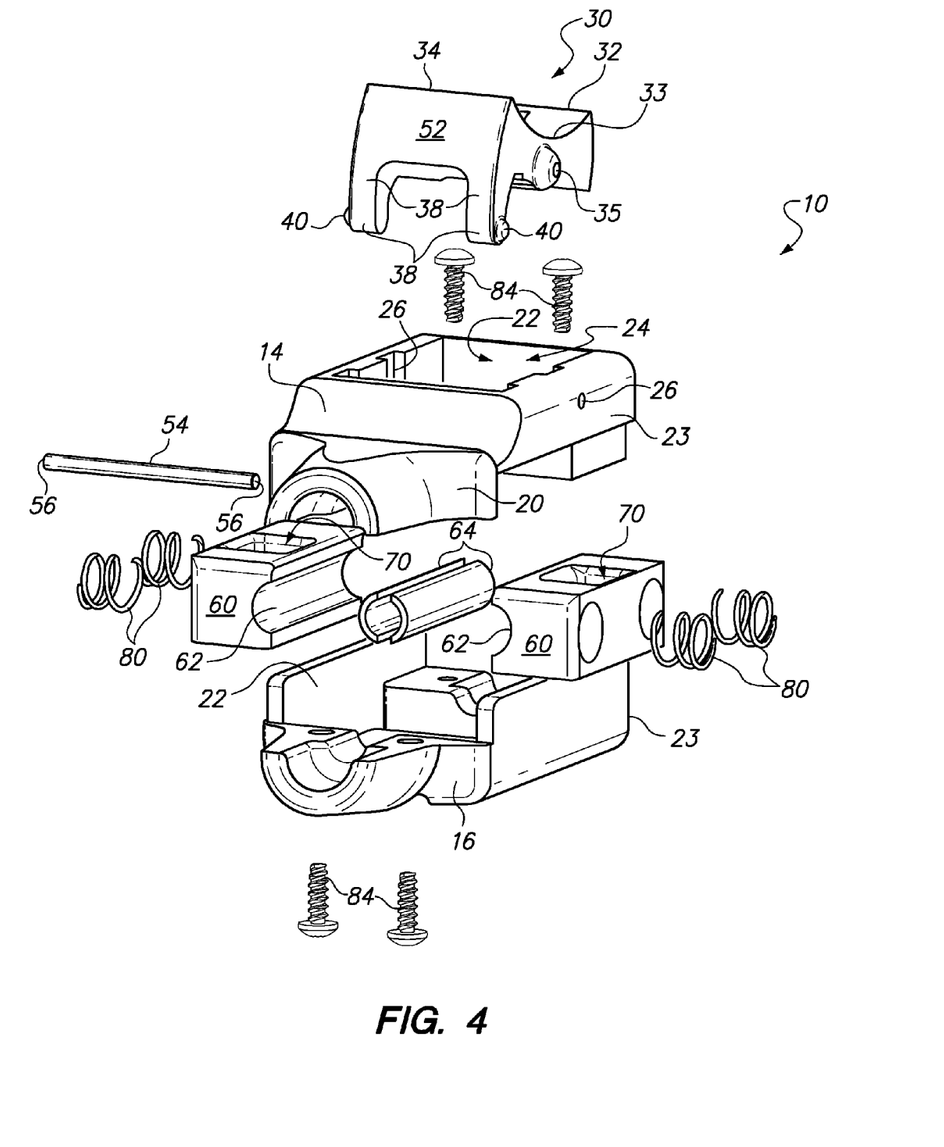
FIG. 4 is a detailed view of a locking device constructed according to one embodiment of the disclosed inventions.

FIG. 4 illustrates a detailed view of the locking device 10 according to the disclosed inventions. The locking device 10 includes the housing 12 having first portion 14 and second portion 16 connected by screws 84, for example, as shown in FIG. 3A. Further, the first 14 and second 16 portions of the housing 12 may be connected using mechanical fastening, interlocking geometries, hinged locks, adhesive, thermal bonding or the like, or combinations thereof. Alternatively, the housing 12 may include or be formed of a single and unitary housing component (not shown). The housing 12 further includes an outer surface 20 and an inner surface 22 defining at least two lateral walls 23. The first portion 14 of the housing 12 having a cavity 24 shaped and sized to receive the actuator 30. The first portion 14 of the housing 12 further includes at least two orifices 26 at the respective lateral walls 23 for placement of the connector ends 56. Preferably, the connector 54 is perpendicularly disposed relative to the passageway 18 of the locking device 10.

In the illustrated embodiment, the actuator 30 includes a proximal portion 32, a distal portion 34 and a middle portion 33 therebetween. For example, actuator 30 has a rocker button configuration but the actuator 30 may have any suitable mechanical linkage configuration, such as a button, a toggle, a push-button, a slide-switch, or the like, or combinations thereof. Middle portion 33 of the actuator 30 rocker button configuration defines a concave outer surface between the proximal portion 32 and the distal portion 34. The middle portion 33 of the actuator 30 includes a passage 35 where the connector 54 is disposed, the connector 54 defining a pivot axis for the actuator 30. The proximal portion 32 and the distal portion 34 of the actuator 30 are configured to move about the pivot axis from a first position (i.e. locked position), so that the locking device 10 engages the elongate member 110, to a second position (i.e. unlocked position), so that the locking device 10 disengages from the elongate member 110 and vice versa.

Further, the actuator 30 includes two arms 36 extending downwardly from the distal portion 34; each arm 36 includes a respective end tip 38 and a side protrusion 40. The arms end tips 38 and the side protrusions 40 of the actuator 30 are configured to be received by a respective engaging member 60, particularly, by a respective slot 70 of the engaging members 60.

The locking device 10 further includes at least two engaging members 60. The engaging members 60 have an elongate configuration and are longitudinally disposed within the housing 12 and are operatively coupled to the actuator 30. The engaging members 60 comprise a respective elongate block configuration having concave side surfaces 62 comprising a respective contact member 64 configured to engage the elongate member 110 when the actuator 30 is in the first position. The engaging members 60 further comprise a respective slot 70; each slot 70 is shaped and sized to receive the respective arms 36 of the actuator 30 when the actuator is in the second position. The engaging members 60 are biasedly disposed towards the passageway 18 and away from the respective lateral walls 23 of the locking device 10. For example, the engaging members 60 are spring biased towards the passageway 18 but the engaging members 60 may be biasedly disposed by another type of mechanical pusher, hinge or combination thereof. The spring biased engaging members 60 are each operatively coupled to one or more springs 80, where the springs 80 are disposed between the engaging members 60 and the inner surface 22 of the respective lateral walls 23 of the housing 12. In one embodiment, having the engaging members 60 biasedly disposed towards the passageway 18 allows the locking device 10 to receive or accommodate a range of different elongate members 110 (e.g. variations in shape, diameter and/or configurations). Further, having at least two engaging members 60 biasedly disposed towards the passageway 18 assist the locking device 10 to translate along and/or rotate about the elongate member 110 with minimal friction or non-friction to the elongate member 110, when the locking device 10 is disengaged (i.e. unlocked position).

The engaging members 60 may directly or indirectly contact the elongate member 110 when the actuator 30 is in the first position. For example, the concave side surfaces 62 of the engaging members 60 may contact the elongate member 110 (direct) or the contact members 64 may contact to the elongate member 110 (indirect). The concave side surfaces 62 and contact members 64 of the engaging members 60 further include an elongate configuration (FIG. 4) so that when the actuator 30 is in the first position, the area of contact with the elongate member 110 is distributed along a section or portion of the elongate member 110, avoiding localized clamping of the elongate member 110. The concave geometry of the side surfaces 62 and/or contact members 64 may be achieved with a singular surface or through the use of multiple contact points that together form a concave like geometry.

Alternatively, the side surface 62 and/or contact member 64 may include other forms and geometrical shapes, for example, a straight surface that conforms to or partially conforms to the elongate member 110 when the locking device 10 is engaged. Additionally, the side surface 62 and/or contact member 64 may include other geometrical configurations and/or features, such as patterned (FIGS. 5C-D) or non-patterned (FIG. 5E) reliefs, cutouts, protrusions or combinations thereof to assist with the engagement of the elongate member 110. Having a patterned or non-patterned reliefs, cutouts, protrusions or combinations thereof, on the surface 62 and/or contact members 64 may be desirable in applications or environments where lubrication and/or fluid are present. Such features may behave like treads on a car tire where the reliefs provide a place for the fluid to migrate, resulting in an increased traction or friction of the engaging members 60 (e.g. surface 62 and/or contact members 64) with the elongate member 110. Examples may include textured surfaces like emery cloth, diamond reliefs, use porous materials or porous absorbent material.

Figure 5A:
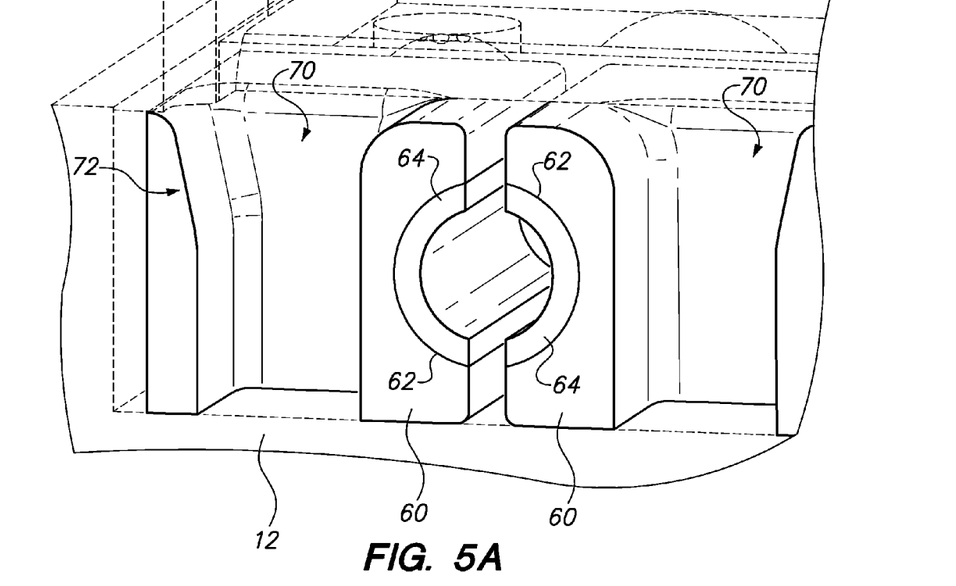
FIGS. 5A-E are perspective and cross-sectional views of locking device portions constructed according to various embodiments of the disclosed inventions.
Figure 5B:
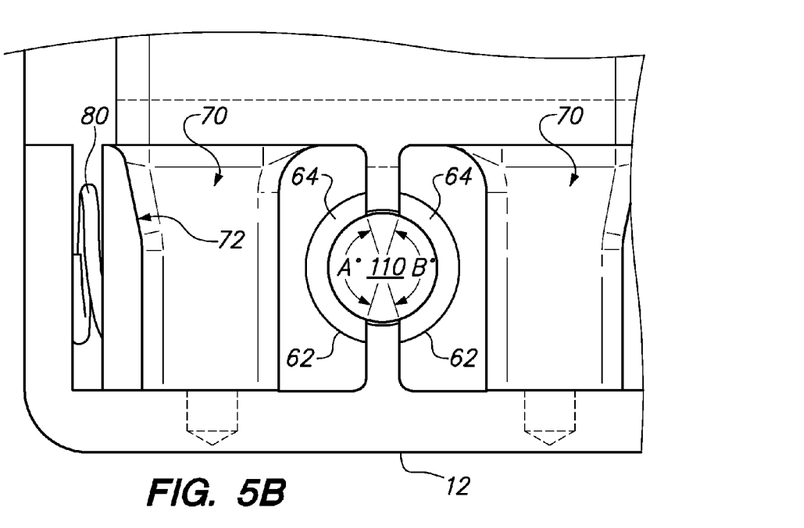
Figure 5C:
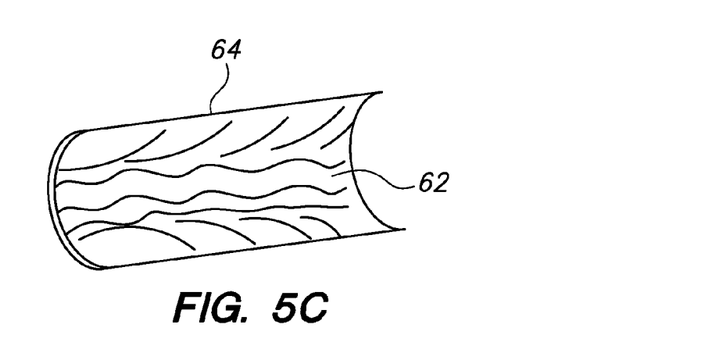
Figure 5D:
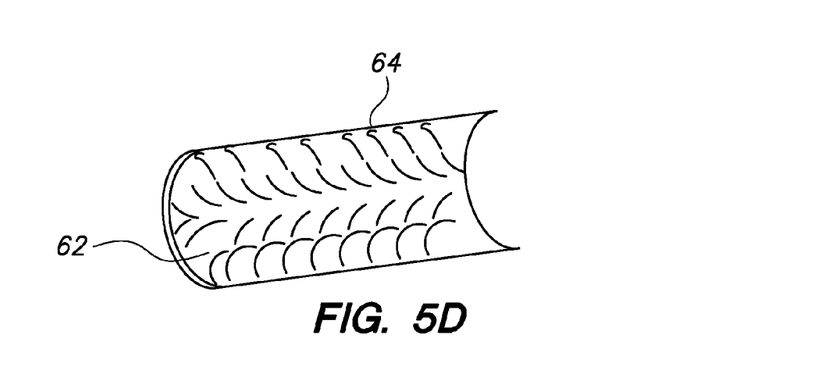
Figure 5E:
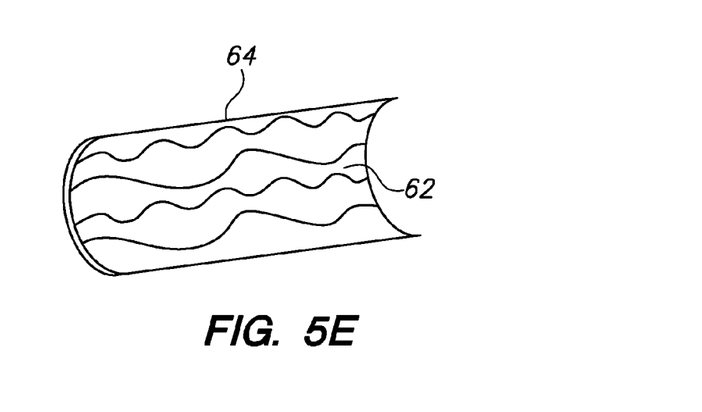

FIGS. 5A-B illustrate the engaging members 60 in the respective spring biased position, according to the disclosed inventions. The engaging members 60 having concave side surfaces 62 may include a respective contact member 64. Each of the contact members 64 include an elongate semi-tubular configuration, as also shown in FIG. 4, composed of a suitable polymeric material or combination thereof. For example, the contact members 64 are made of a material having a shore durometer range between A40 to A100, preferably, about A50. Each of the contact members 64 are directly or indirectly coupled, attached or secured to a respective concave side surface 62 of the engaging members 60, for example, by adhesive, thermal bonding or the like, interlocking geometries, mechanical fastening or combinations thereof. Further, the slots 70 of the engaging members 60 are configured to receive the respective arms 36 of the actuator 30 when the actuator is in the second position. The slots 70 include a respective sloped matting surface 72 (i.e. ramp geometry) configured to receive respective arm side protrusions 40.

When the actuator 30 is in the first position and from a perspective view of a plane perpendicular to the passageway 18, the contact of the engaging members 60 (e.g. side surfaces 62 or contact members 64) with the elongate member 110 may be between an aggregate angle range of 240° to 340° degrees (A°+B°), as shown in FIG. 5B. For example, when the engaging members 60 (e.g. side surfaces 62 or contact members 64) are composed of materials configured to conform to a surface of the elongate member 110, having an aggregate angle larger than 340° may create undesirable excessive compressed material or pinch points that can accumulate between the engaging members 60 when the device 10 is engaged (i.e. locked). In one embodiment, a preferred aggregate angle of contact of the engaging members 60 (e.g. side surfaces 62 or contact members 64) with the elongate member 110 is about 290° (A°+B°), as shown in FIG. 5B.

Figure 6A:
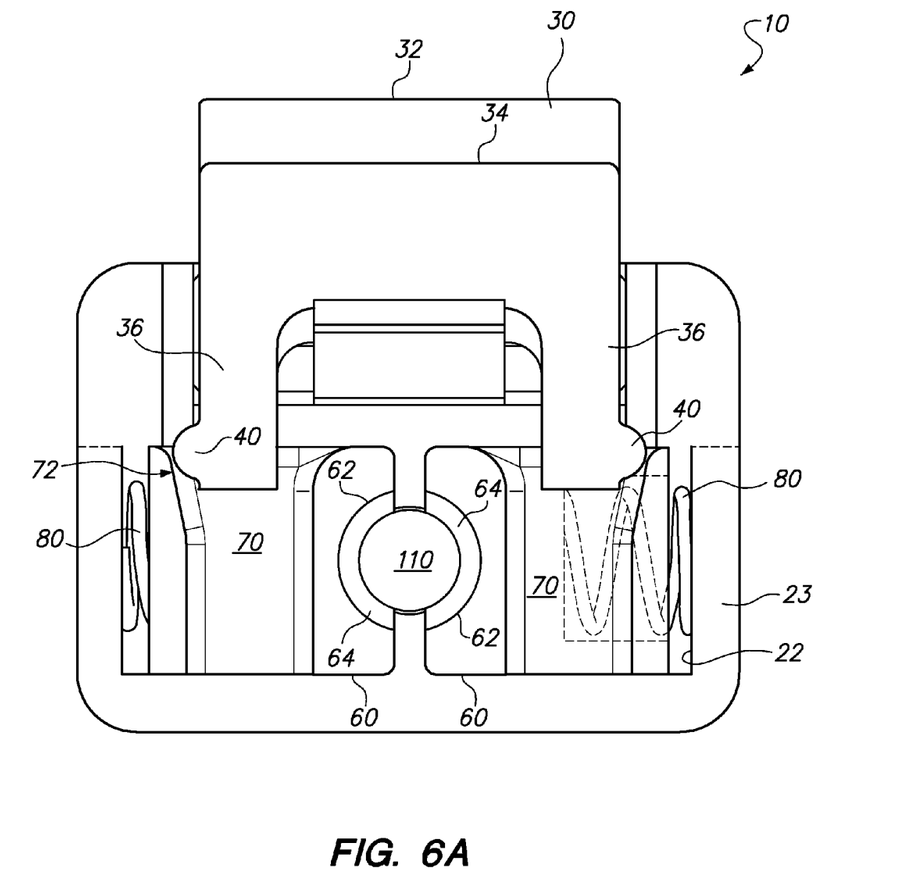
FIGS. 6A-D are cross-sectional views of a locking device constructed according to various embodiment of the disclosed inventions.

FIG. 6A illustrates the engaging members 60 in their biased position when the actuator 30 is in the first (locked or engaged) position, according to the disclosed inventions. In the first position of the actuator 30, the proximal portion 32 of the actuator 30 is moved, pressed, or pushed downwardly towards the housing 12, so that the arms 36 are positioned at the opening of the slots 70 or out of the slots 70, without displacing the engaging members 60 from their spring biased position that engages the elongate member 110.

Figure 6B:
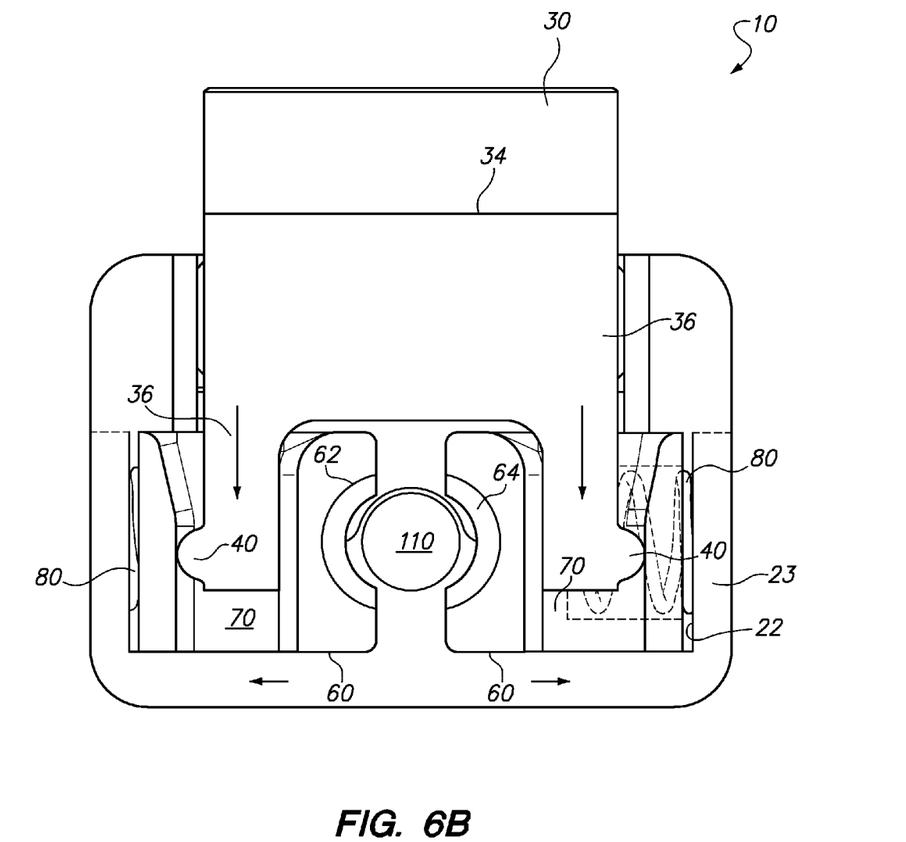

FIG. 6B illustrates the engaging members 60 displaced from their biased position when the actuator 30 is in the second (unlocked or disengaged) position, according to the disclosed inventions. In the second position of the actuator 30, the distal portion 34 of the actuator 30 is moved, pressed, or pushed downwardly towards the housing 12 so that the arms 36 are received within the slots 70 of a respective engaging member 60, displacing the engaging members 60 from the spring biased position towards the respective lateral walls 23 of the housing 12 to thereby disengage the locking device 10 from the elongate member 110. Each of the arm side protrusions 40 comprise a spherical, semi-spherical, or convex configuration, or any other suitable configuration, so that when the actuator 30 moves towards the second position, the side protrusions 40 slide downwardly the respective sloped matting surfaces 72, displacing the engaging members 60 towards the respective lateral walls 23 (i.e. inner surface 22) of the housing 12 and away from the passageway 18. For example, the displacement of each of the engaging members 60 towards the lateral walls 23 is approximately 0.075 inches or less.

Figure 6C:
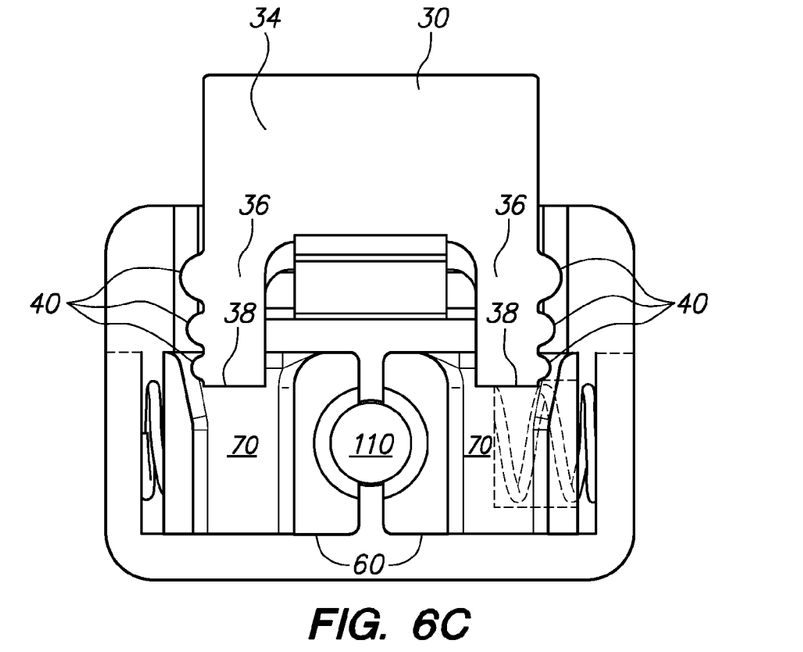
Figure 6D:
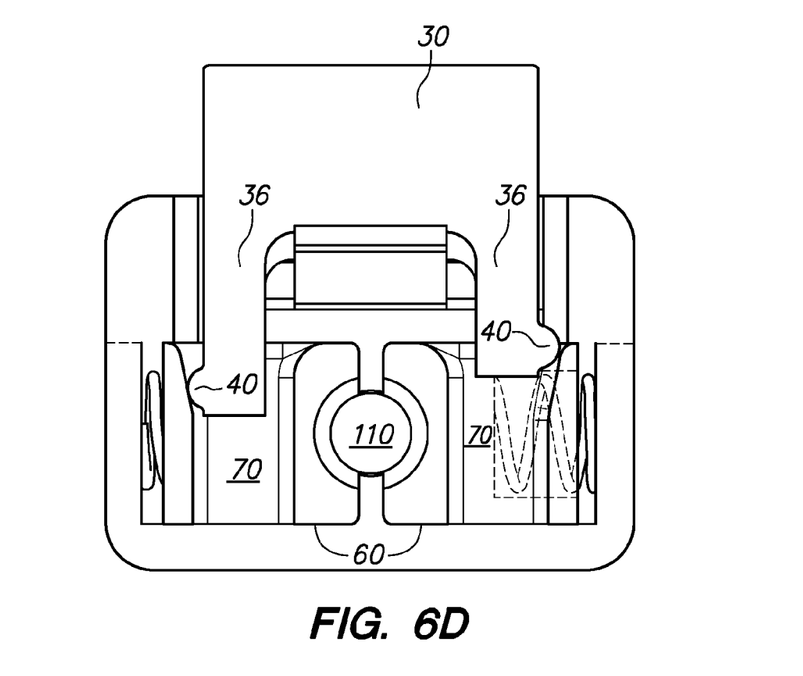

Alternatively, each arm 36 may include one or more protrusions 40, as shown in FIG. 6C. For example, the plurality of protrusions 40 may vary in size from smaller at the end tips 38 to larger towards the distal end 34 of the actuator 30. In another alternative embodiment, the arms 36 of the actuator 30 may be stagger or offset, as for example shown in FIG. 6D, where one of the arms 36 is longer than the other arm 36.

Figure 7A:
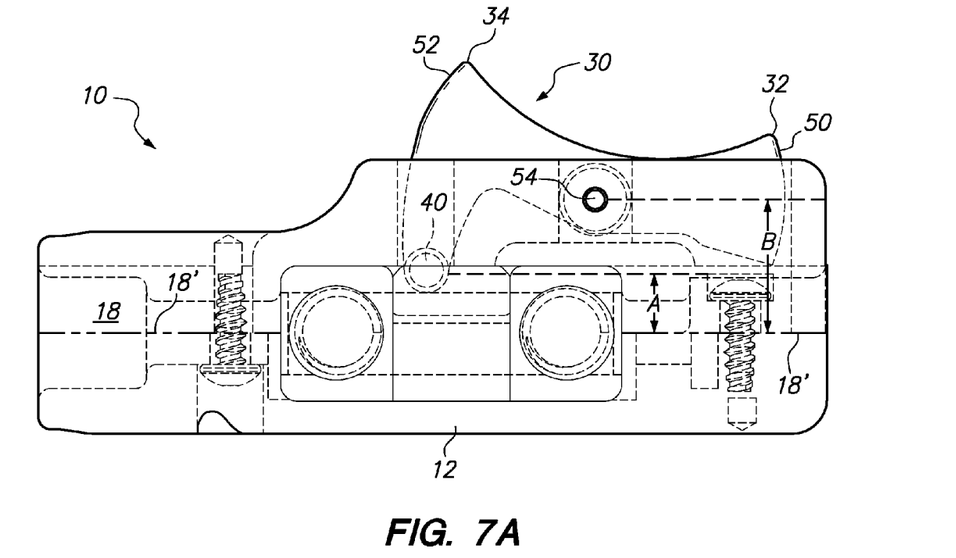
FIGS. 7A-B are cross-sectional views of a locking device constructed according to one embodiment of the disclosed inventions.
Figure 7B:
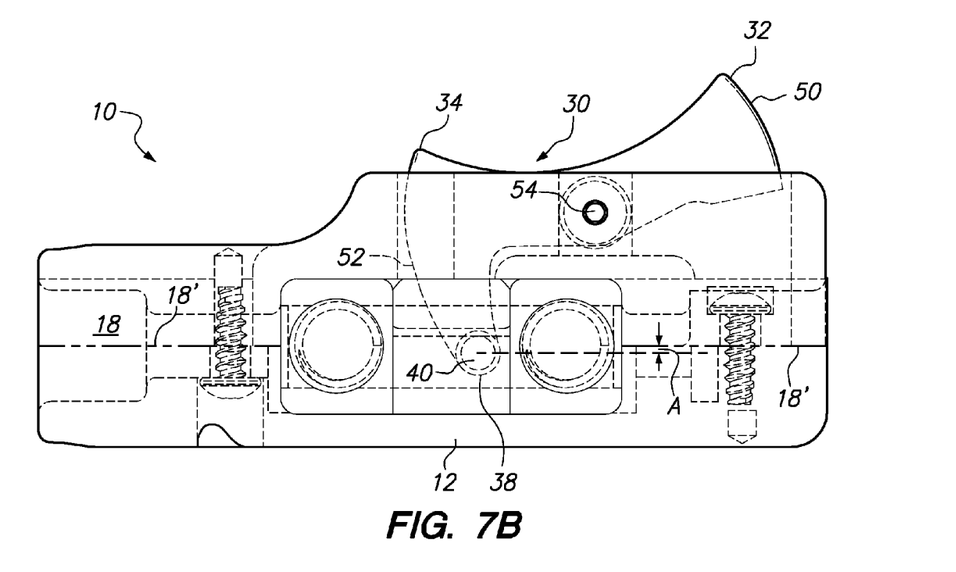

FIG. 7A further illustrates the actuator 30 in the first (locked or engaged) position, according to the disclosed inventions. The actuator 30 includes a proximal arcuated configuration 50 extending from the proximal end 32 and a distal arcuated configuration 52 extending from the distal end 34 to the arms end tips 38. The arcuated configurations 50 and 52 allow the actuator 30 to move in a substantial arc type motion having an angular range of motion, for example, between 10° to 40°. As shown under "A", the arms side protrusions 40 are offset from the passageway 18 central axis 18', for example, by approximately 0.175 inches or less. Also, as shown under "B", the connector 54 pivot axis is offset from the central axis 18' of the passageway 18, for example, by approximately 0.5 inches or less. FIG. 7B further illustrates the actuator 30 in the second (unlocked or disengaged) position, according to the disclosed inventions. The distal arcuated configuration 52 of the actuator 30 moves downwardly in a substantial arc type motion, so that the arms 36 of the actuator 30 are received within the slots 70 of a respective engaging member 60, displacing the engaging members 60 from the spring biased position, and therefore unlocking and disengaging the locking device 10 from the elongate member 110. Further, as shown under "A", the arms side protrusions 40 are offset from the central axis 18' of the passageway 18, for example, by approximately 0.025 inches or less. The offset of 0.025 inches or less allows displacement of the engaging members 60 from their biased position so that the locking device 10 exerts minimal friction or non-friction to the elongate member 110, when the locking device 10 is disengaged or unlocked.

Figure 8A:
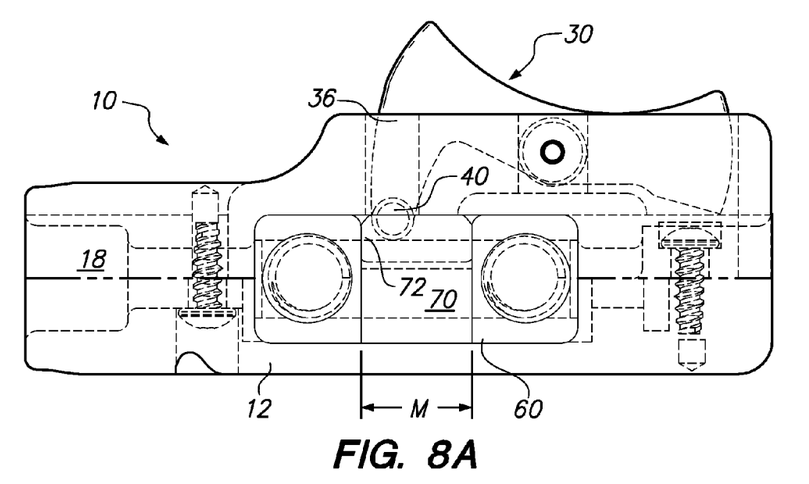
FIGS. 8A-B are cross-sectional views of a locking device constructed according to one embodiment of the disclosed inventions.
Figure 8B:
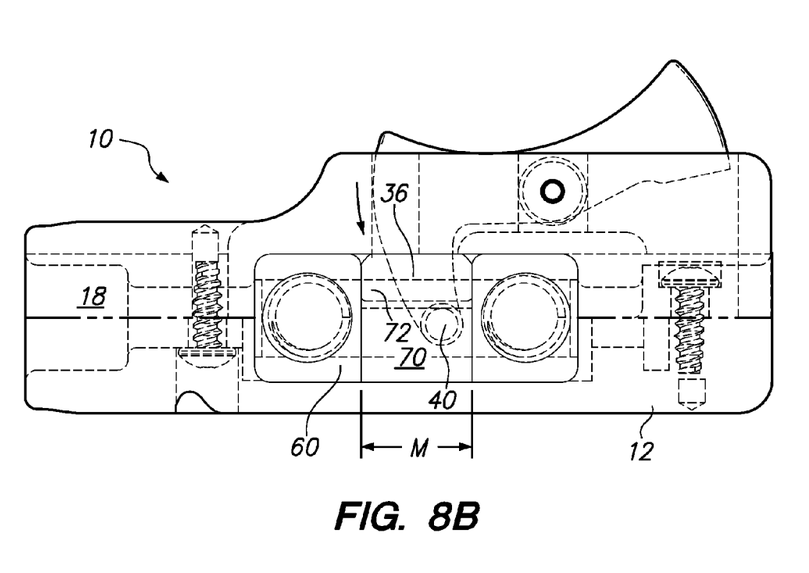

According to the disclosed inventions, during the arc type motion or range of motion of the actuator 30 from the first (locked or engaged) position, shown in FIG. 8A, to the second (unlocked or disengaged) position shown in FIG. 8B, the arms 36 and protrusions 40 are disposed, moved or translated within the slots in a middle portion of the engaging members 60, as shown under "M". Each of the arm side protrusions 40 slide downwardly the respective sloped matting surfaces 72 of the slots 70 in the middle region "M" of the engaging members 60 (FIG. 8B), displacing the engaging members 60 from their spring biased position towards the respective lateral walls 23 (i.e. inner surface 22) of the housing 12 and away from the passageway 18 (FIGS. 6B and 8B). Having the arms 36 and protrusions 40 disposed within the middle region "M" of the engaging members 60, allows the application of relative low force to the actuator 30 to be moved from the first to the second position and vice versa (e.g. approximately 2.4 lbf to disengage and approximately 1.2 lbf to engage), and further allows the engaging members 60 to be displaced from their spring biased position without titling the engaging members 60 and creating friction to the elongate member 110, when the locking device 10 is disengaged or unlocked.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A slidable locking device, comprising:
a housing having a passageway therethrough;
an actuator coupled to the housing and movable between a locked position and an unlocked position, the actuator having at least two arms extending therefrom; and
at least two engaging members disposed within the housing and operatively coupled to the actuator, each engaging member having a slot configured to receive a respective arm of the actuator, and wherein the engaging members are biased towards the housing passageway, and the engaging members are disposed toward the housing passageway when the actuator is in the locked position, and the engaging members are disposed away from the housing passageway when the actuator is in the unlocked position,
the device further comprising a connector coupled between the housing and the actuator, wherein the connector defines a pivot axis and the actuator is configured to move about the pivot axis between the locked position and the unlocked position.

2. The slidable locking device of claim 1, wherein the actuator is movable between the locked position and the unlocked position by an application of force in a range between about 1 lbf to about 3 lbf.

3. The slidable locking device of claim 2, wherein the actuator is movable from the unlocked position to locked position by an application of force of about 1.2 lbf, and wherein the actuator is movable from the locked position to unlocked position by an application of force of about 2.4 lbf.

4. A slidable locking device, comprising:
a housing having a passageway therethrough;
an actuator coupled to the housing and movable between a locked position and an unlocked position, the actuator having at least two arms extending therefrom; and
at least two engaging members disposed within the housing and operatively coupled to the actuator, each engaging member having a slot configured to receive a respective arm of the actuator, and wherein the engaging members are biased towards the housing passageway, and the engaging members are disposed toward the housing passageway when the actuator is in the locked position, and the engaging members are disposed away from the housing passageway when the actuator is in the unlocked position, and
wherein each of the engaging members comprises one or more sloped mating surfaces defining the respective slot, and each arm of the actuator comprises one or more protrusions, and wherein the one or more protrusions are configured to engage the respective one or more sloped mating surfaces.

5. The slidable locking device of claim 4, wherein each of the one or more protrusions has a spherical, semi-spherical, or convex configuration.

6. The slidable locking device of claim 4, wherein the one or more protrusions are configured to slide along the respective one or more sloped mating surfaces so that the actuator arms exert force against and thereby move the engaging members outwardly away from the housing passageway.

7. The slidable locking device of claim 2, wherein the housing is an elongated housing having a first portion and a second portion, the first and second portions defining an internal cavity, and wherein the at least two engaging members are disposed within the cavity.

8. A medical device for treating a target site in a body of a patient, comprising:
an elongate member having a proximal portion, a distal portion, and a lumen extending therebetween; and
a locking device slidably disposed on the elongate member, the locking device comprising
a housing having a passageway therethrough;
an actuator coupled to the housing and movable between a locked position, wherein the locking device is engaged to the elongate member, and an unlocked position, wherein the locking device is disengaged from the elongate member, the actuator having at least two arms extending therefrom that are operatively coupled with a corresponding at least two engaging members disposed within the housing, each engaging member having a slot configured to receive a respective arm of the actuator, wherein the engaging members are biased towards the housing passageway into engagement with the elongate member when the actuator is in the locked position, and wherein the engaging members are disposed away from the housing passageway and elongate member when the actuator is in the unlocked position, and
wherein each of the engaging members comprises one or more sloped mating surfaces defining the respective slot, and each arm of the actuator comprises one or more protrusions, and wherein the one or more protrusions are configured to engage the respective one or more sloped mating surfaces.

9. The medical device of claim 8, wherein the locking device resists relative movement with respect to the elongate member when the actuator is in the locked position.

10. The medical device of claim 8, wherein the locking device is configured to translate along the elongate member and to rotate about the elongate member when the actuator is in the unlocked position.

11. The medical device of claim 8, wherein the one or more protrusions are configured to slide along the respective one or more sloped mating surfaces so that the actuator arms exert force against and thereby move the engaging members outwardly away from the housing passageway.

12. The medical device of claim 8, wherein the engaging members comprise concave surfaces to engage an arcute surface the elongate member.

13. The medical device of claim 8, wherein the engaging members comprise a compliant material configured to conform to a surface of the elongate member.

14. The medical device of claim 8, wherein the locking device is configured to apply a force to the elongate member in a range of about 10 PSI to about 40 PSI when the actuator is in the locked position.

15. The medical device of claim 14, wherein the locking device is configured to apply a force to the elongate member in a range of about 12 to about 17 PSI when the actuator is in the locked position.

16. The medical assembly of claim 15, wherein the locking device is configured to distribute the applied force to the elongate member such that the lumen of the elongate member maintains patency.

17. The medical device of claim 8, wherein the locking device is configured to withstand an aggregate load in a range of between about 4 lbf to about 12 lbf without any substantially movement relative to the elongate member when the actuator is in the locked position.

* * * * *